US006605308B2

(12) United States Patent
Shane et al.

(10) Patent No.: US 6,605,308 B2
(45) Date of Patent: Aug. 12, 2003

(54) PATHOGEN MANAGEMENT SYSTEM

(75) Inventors: Tommy J. Shane, Loganville, GA (US); Harvey Swain, Lawrenceville, GA (US)

(73) Assignee: Tomoco$_2$ Equipment Company, Loganville, GA (US)

(*) Notice: Subject to any disclaimer, the term of this patent is extended or adjusted under 35 U.S.C. 154(b) by 0 days.

(21) Appl. No.: 10/050,492

(22) Filed: Jan. 16, 2002

(65) Prior Publication Data
US 2002/0134317 A1 Sep. 26, 2002

Related U.S. Application Data
(60) Provisional application No. 60/261,923, filed on Jan. 16, 2001, and provisional application No. 60/316,047, filed on Aug. 30, 2001.

(51) Int. Cl.$^7$ .............................................. A23L 3/34
(52) U.S. Cl. .................. 426/332; 426/532; 452/123; 452/131; 134/25.3; 134/26
(58) Field of Search ................ 426/332, 532; 452/123, 131; 134/25.3, 26

(56) References Cited

U.S. PATENT DOCUMENTS

| | | | | | |
|---|---|---|---|---|---|
| 3,958,020 | A | * | 5/1976 | deVries | 426/264 |
| 4,244,978 | A | * | 1/1981 | Barta | 426/332 |
| 4,250,144 | A | * | 2/1981 | Ratigan | 210/754 |
| 4,313,827 | A | * | 2/1982 | Ratigan et al. | 210/136 |
| 4,333,833 | A | * | 6/1982 | Longley et al. | 137/888 |
| 4,362,753 | A | * | 12/1982 | Barta | 426/332 |
| 4,573,119 | A | * | 2/1986 | Westheimer et al. | 713/190 |
| 4,769,154 | A | * | 9/1988 | Saylor et al. | 210/707 |
| 4,996,741 | A | * | 3/1991 | Covell, III | 452/131 |
| 5,118,426 | A | * | 6/1992 | Duncan et al. | 210/721 |
| 5,120,452 | A | * | 6/1992 | Ness et al. | 210/721 |
| 5,178,579 | A | * | 1/1993 | Simmons | 452/123 |
| 5,234,703 | A | * | 8/1993 | Guthery | 134/25.3 |
| 5,364,650 | A | * | 11/1994 | Guthery | 134/25.3 |
| 5,935,518 | A | * | 8/1999 | Richard et al. | 210/764 |
| 6,019,905 | A | * | 2/2000 | Waggoner | 210/739 |
| 6,083,095 | A | * | 7/2000 | Simmons | 452/123 |
| 6,093,093 | A | * | 7/2000 | Mostoller et al. | 452/123 |
| 6,220,952 | B1 | * | 4/2001 | Taylor, Sr. et al. | 452/123 |

FOREIGN PATENT DOCUMENTS

GB 1428920 * 3/1976

OTHER PUBLICATIONS

Emswiler–Rose et al. 1984. J. of Food Science 49:931.*
Odlaug et al. 1978. J of Food Science 43:964.*
Johnson et al. 1979. J of Food Science 44:169.*
Ghanbari et al. 1981. J of Food Science 47:185.*
Romans & Ziegler, 1977. The Meat We Eat. The Interstate Printers & Publishers, Inc., p. 22,23,56, 57, 118 ,123, 124, 131≃≃197, 198, 199,200.*

* cited by examiner

Primary Examiner—Carolyn Paden
(74) Attorney, Agent, or Firm—Thomas, Kayden, Horstemeyer & Risley, LLP; Todd Deveau

(57) ABSTRACT

A system to control pathogens on a target element is disclosed, wherein the target element is subjected to hypochlorous acid. The present invention incorporates the use of hypochlorous acid as a pathogen control medium, wherein a hypochlorous acid stream of between about 4.3 and 7.0 pH as a pathogen reduction agent is utilized. In one embodiment, the hypochlorous acid stream is used to reduce pathogens in poultry processing plants.

32 Claims, 4 Drawing Sheets

PATHOGEN MANAGEMENT SYSTEM

RELATED U.S. APPLICATION

This application claims priority from U.S. Provisional Application No. 60/261,923 filed Jan. 16, 2001, and U.S. Provisional Application No. 60/316,047 filed Aug. 30, 2001, both incorporated herein by reference.

BACKGROUND OF THE INVENTION

1. Field of the Invention

This invention relates generally to the field of disinfectants, and relates more specifically to using hypochlorous acid solutions as pathogen management systems in, for example, a poultry processing system to limit poultry contamination.

2. Background of the Invention

Chlorination is known method for killing undesirable microorganisms. Chlorine may be provided in multiple forms including chlorine gas ($Cl_2$), sodium hypochlorite liquid, calcium hypochlorite powder or granules, or isocyurantes. Chlorine gas ($Cl_2$) is a relatively cheap and highly effective antimicrobial agent; however, it is also a highly toxic and corrosive gas. Hypochlorites such as NaOCl or $Ca(OCl)_2$ are a much safer alternative, but are considerably more expensive that gaseous chlorine. Finally, hypochlorite solutions (i.e., bleach) may also be utilized, however these are rarely used in large scale Water treatment applications because they are bulky and expensive. Regardless of the chlorine source, hypochlorous acid (HOCl) and the hypochlorite ion ($OCl^-$) are the final desirable antimicrobial products.

One method of forming HOCl occurs when $Cl_2$ is dissolved in water. The reaction proceeds according to the following equation:

$$Cl_2 + H_2O \Leftrightarrow HOCl + H^+ + Cl^- \tag{1}$$

Another method for producing HOCl uses metal hypochlorites dissolved in water. The reaction proceeds according to the following equation:

$$NaOCl + H_2O \Leftrightarrow NaOH + HOCl \tag{2}$$

This method is generally utilized by common household hypochlorites and generates HOCl on a relatively small scale.

HOCl is a weak acid and will dissociate. In aqueous solution, HOCl and $OCl^-$ are generally present in a pH dependent equilibrium:

$$HOCl \Leftrightarrow H^+ + OCl^- \quad pKa = 7.53 \tag{3}$$

At low pH, HOCl is the predominant form, while at high pH, $OCl^-$ predominates. The HOCl form is about 80 times more effective than $OCl^-$ for killing microorganisms because HOCl crosses cell membranes easier than the hypochlorite ion. Accordingly, it would be desirable to control the pH of the chlorinated solution to increase the antimicrobial effectiveness of the chlorination process.

One particular use of chlorination is to kill undesirable microorganisms in poultry processing systems. Since much of the poultry processing involves moving the bird on conveyers and human contact, provisions must be made to keep both the equipment and personnel sanitized.

For example, Salmonella is one of the most important causes of foodborne disease worldwide. In many industrialized countries the incidence of salmonellosis in humans and the prevalence of Salmonella in many food products have increased significantly over the last twenty years. Salmonella bacteria have a broad host-spectrum, and can be isolated from a wide range of animal species, including birds and reptiles. The animals usually are healthy carriers, and contaminated feed plays an important role in the epidemiology 5 of salmonellosis. Salmonella can survive for a long time in the environment. Humans are usually infected through consumption of contaminated foods of animal origin. However, other food such as fresh produce, seafood and chocolate have also been implicated in outbreaks because of cross-contamination, use of contaminated water, use of manure as a fertilizer, presence of animals or birds in the production area or other factors.

In a typical poultry processing operation, freshly laid fertile eggs are collected and incubated. After they hatch, chicks are delivered to farms, reared until ready for slaughter and then transported to a processing plant. At the plant, the process of slaughtering includes several phases from unloading and shackling the live birds to grading and packaging the carcasses. Then, carcasses are shipped and distributed chilled or frozen while some poultry carcasses are used for portioning and/or to produce a variety of raw or processed products. The microbiological condition of poultry carcasses is highly dependent on the manner in which animals are reared and slaughtered. The microbiological condition of live birds influences the microbiology of the products and the live animals are the principal source of microorganisms found on poultry carcasses. At the processing plant, the conditions of slaughtering will further influence the extent to which processed poultry will be contaminated.

There are many sources of contamination during poultry processing. Commercially grown poultry flocks are collected on the farm, placed into crates, transported to the processing plant and slaughtered on the same day. Contaminated crates can be a significant source of Salmonella and *E. coli* on processed carcasses. Contamination of feathers with microorganisms of fecal origin increases as birds are confined in crates for transport to the plant and microorganisms in feces and on feathers can be spread from bird to bird within the crates. Stress of transportation may amplify the pathogen levels. In one study, fecal droppings collected in broiler houses about one week prior to slaughter were contaminated at a rate of 5.2% while Salmonella was found in 33% of the samples collected from live-haul trucks at the processing plant.

During hanging, as feathers, feet and bodies are contaminated with a variety of bacteria, wing flapping creates aerosols and dust, contributing to contamination of the unloading zone and transmission of pathogens at this stage.

Stunning and killing have few microbiological implications, although electrical waterbath stunning may lead to inhalation of contaminated water by the birds and microbial contamination of carcass tissues.

During scalding, soil, dust and fecal matter from the feet, feathers, skin and intestinal tract are released into the scald water and thus provide a significant opportunity for cross contamination. A large variety of bacteria, e.g. Salmonella, Staphylococcus, Streptococcus, Clostridium spp. have been isolated from scald water or from carcasses or air sacs immediately after scalding.

Bacterial survival in the scald water is influenced by scald temperature and time. The lethal effect of water held at 60° C. (hard scald) used for carcasses intended for water chilling is measurable and greater than the lethal effect of water held at lower temperatures, e.g. 50–52° C. (soft scald) as used for carcasses that will be air chilled.

It has also been demonstrated that scalding results in modifications to the poultry skin: removal or damage of the epidermal layer, exposing a new surface for contamination which is smoother and less hydrophobic, exposure of microscopical channels and crevices. During and after scalding, the skin surface retains a film of scalding water which contains organic matter and large numbers of bacteria. Some of these bacteria may adhere more easily to the modified surface of the skin. Some may be retained in the channels or crevices on the skin surface as well as in the feather follicles. During the following stage of defeathering, there may be entrapment of bacteria in the channels, crevices and follicles. When entrapped, the bacteria may be difficult to remove by subsequent procedures, including mechanical and chemical decontamination treatments; they also display greater heat resistance.

Defeathering with automatic machinery may be expected to cause considerable scattering of microorganisms in particular via aerosols. Early findings, from work being carried out in the United Kingdom, indicate that these aerosols from defeathering can be reduced by altering the design of the equipment. Conditions inside the machines are favorable to the establishment of a biofilm and colonization by pathogens, in particular *S. aureus* which can survive, multiply and become indigenous to the equipment. Defeathering has been recognized as a major source of carcass contamination with *S. aureus*, Salmonella, Campylobacter spp and *E. Coli*. Several studies have established that the microbial populations on poultry carcasses reflect the microbiological condition of the carcasses immediately after defeathering.

Evisceration can give rise to fecal contamination with enteric pathogens such as Salmonella, Campylobacter and Cl. perfringens, especially when intestines are cut and/or when automatic machines are not set properly. In addition, microorganisms may be transferred from carcass to carcass by equipment, workers, and inspectors.

Spray washing of carcasses removes visible fecal contamination and some microorganisms such as Salmonella and *E. Coli*. However, it does not eliminate those bacteria that have become attached to the carcass surface or entrapped in the inaccessible sites of the skin surface. It has been demonstrated that continuous carcass washing or applying a series of sprays at the various stages of evisceration removes bacteria before they are retained, and this is much more effective than a single wash after evisceration. There is a danger that use of water sprays, in particular those used in carcass washing, may create aerosols that can spread microbiological contamination.

Three types of chilling processes may be used: air blast, water immersion and a combination of air and water chilling. All three methods may lead to some degree of cross contamination. With regard to the final microbiological load on the carcass, it has been demonstrated that properly controlled water immersion chilling can reduce overall levels of carcass contamination. However, high levels of contamination of carcasses before chilling and insufficient water used per carcass (amount of fresh water replacement; number of carcasses in relation to the volume of chilled water) may result in an increase in the level of microbial contamination on carcasses rather than a decrease.

There have been numerous studies to determine the relative effect of each processing step on carcass contamination. Generally, the results show that aerobic plate counts or count of Enterobacteriaceae decrease during processing.

The data on the prevalence of Salmonella contaminated carcasses are highly variable. The proportion of contaminated carcasses appears to be influenced mainly by the condition of incoming birds and also by processing. Although the prevalence of Salmonella contaminated carcasses can be high, the number of Salmonella per carcass is usually quite low. In comparison with Salmonella, campylobacters are generally carried in high numbers by poultry. Therefore carcasses are more readily contaminated during processing and the numbers present are correspondingly higher.

Antimicrobial compounds have been used for disinfecting products and equipment surfaces for many years. Some of the antimicrobial compounds that have been approved for use are: hot water, steam, lactic acid spray, acetic acid spray, citric acid spray, trisodium phosphate, chlorine dioxide, acidulated sodium chlorite, and sodium hypochlorite (bleach). Hot water is generally not used with poultry products because hot water can scorch surfaces, resulting in a "cooked" appearance. This is especially crucial if the end product is to be deboned unfrozen or fresh breast fillets. Steam pasteurization procedures have recently been developed and have been shown to be very effective against bacteria; however, applying steam to individual carcasses moving down a processing line at 70 to 140 carcasses per minute is challenging. Thus, the industry has been slow to incorporate this type of treatment.

Organic acids are excellent for killing bacteria because they penetrate and disrupt the cell membrane and dissociate the acid molecule, thereby acidifying the cell contents. They are stable in the presence of organic material, such as blood or feces and they are fairly inexpensive to use. Acids are susceptible to water pH problems (such as high incoming water pH), they may cause product defects, such as off flavors, odors, and colors, even when used at low levels. Additionally, organic acids may corrode equipment.

Trisodium phosphate (TSP) is becoming more widely accepted and used, because the USDA is encouraging its use within the industry. TSP is costly to use because of the quantity needed to disinfect carcasses. There are negative aspects to using TSP in poultry processing plants that should be considered. Residual TSP on carcasses causes the chiller water pH to increase dramatically. In plants where TSP is used, the chiller water will generally be in the pH range of 9.7 to 10.5. This is extremely high and completely eliminates the ability of chlorine to become its effective form, hypochlorous acid. Hypochlorous acid forms most effectively when water is in the pH range of 5.5 to 7.0. Thus, plants using TSP may as well be dumping their bleach down the drain. This is not a desired situation because chlorine is very effective against Salmonella. In fact, plants in the Southeastern U.S. that have installed a TSP system have often seen their Salmonella and *E. Coli* prevalence increase when compared to levels prior to using the TSP. This is most likely due to the TSP washing Salmonella off of one carcass and it is then able to spread to other carcasses. Scientists have reported that *Listeria monocytogenes* is resistant to the effects of trisodium phosphate (TSP), and exposure to a high (8%) level of TSP for 10 minutes at room temperature is required to reduce bacterial numbers by 1 $\log_{10}$ after a colony has grown on a surface and a protective layer (biofilm) has been formed.

Chlorine dioxide has been evaluated in processing plants and seems to be effective for killing bacteria at very low concentrations; however, it is expensive to generate and very difficult to maintain at a particular concentration in chiller water. Some USDA inspection personnel have been reticent to allow its use in plants.

Sodium hypochlorite (bleach) is by far the most widely used chemical sanitizer in the poultry industry. It is excellent for killing bacteria and is inexpensive; however, as mentioned previously, it forms its most effective bacteriocidal agent, hypochlorous acid, in the pH range of 5.5 to 7.0. Thus, when used in combination with a TSP system, bleach is generally ineffective. Chlorine is inactivated in the presence of organic material. Residual blood and feces in the chiller can greatly affect how well chlorine is able to kill bacteria on carcass surfaces. It is essential to maintain proper flow rate in the chiller to reduce organic material sufficiently to allow the chlorine to be effective.

As discussed, chlorine is available in several forms: gas, liquid, and powder. The choice is usually dependent upon the volume of water to be treated, the amount of disinfection required, and the area in which the chlorine will be used.

Chlorine gas is considered the best choice where large volumes of water are to be chlorinated at high levels (4–5 ppm). Chlorine gas is pure 100% available chlorine, it lowers the pH slightly, and is easy to control and apply. Economically, it is the least expensive source on the basis of available chlorine.

Conventionally, hypochlorites (calcium and sodium) are second in choice because chemical dosage is difficult to control. Hypochlorites raise the pH of the water, which in hard water, may cause deposits on equipment. Hypochlorites are more sensitive to organic matter in water resulting in a faster loss of germicidal power. Being unstable, hypochlorites are difficult to store and deterioration results during storage. Hypochlorites are a good choice, however, when only small amounts are needed, such as localized germicidal application for clean-up and preventing slime formation on belts and other equipment.

Despite the several known processes for producing hypochlorous acid and pathogen management, there remains a need for a quick, safe, and efficient process for producing hypochlorous acid solutions suitable for use as a disinfectant in poultry processing.

SUMMARY OF THE INVENTION

The present pathogen management system improves the conventional art of controlling pathogens on a target element (for example, a poultry product in a poultry processing line) by subjecting the bird to a disinfectant, the improvement comprising subjecting the target element to hypochlorous acid. Preferably, the present invention comprises utilizing a hypochlorous acid stream of between about 4.3 and 7.0 pH as a pathogen reduction agent. For example, the present system preferably can provide a poultry carcass exiting a post chiller of a poultry processing system as clean, or cleaner, both organically and microbially, than the carcass being off line processed using standard FSIS techniques.

As a pathogen management system used with poultry processing, preferably the present invention comprises a three control point approach to pathogen reduction. When a carcass is received into the pick/kill area, many pathogens are present on this carcass. Pathogen control begins in this area by the application of hypochlorous acid. At other locations of the poultry processing, a similar use of hypochlorous acid is applied so the plant can control the pathogen throughout.

The first critical control point is located in the pick/kill room. A first washing system is placed post picking. The first washing system washes the carcasses completely (feet to head) using mechanical brushes and strategically positioned sprays with hypochlorous acid before the carcass enters the processing area. The purpose of this point controls Salmonella, *Escherichia coli* and organics on the exterior of the carcass. This control point helps control the pathogens and organics entering the processing area that are coming from grow-out or farms.

The second critical control point is located after the carcasses have been processed through evisceration. After the final wash system (IOBW), a second washing system is added. The second washing system washes the carcasses completely (hocks to tips of wings) both mechanically and by sprays with hypochlorous acid before the carcass enters the chilling area. The purpose of this point controls Salmonella, *E-Coli* and organics on the interior and exterior of the carcass. This control point also helps control the pathogens and organics entering the chiller area that are coming from evisceration.

A third critical control point is located in the chilling system. This control point is set up to reduce the existing pathogens on and inside the carcass and prevent cross contamination of the carcass in the chiller water. By adding hypochlorous acid to the chillers and maintaining available free chlorine in the chiller water, pathogen control is completed.

Preferably, the hypochlorous acid is generated by a pressurized solution system that produces a carbonic acid solution, using carbon dioxide gas and a make-up water source, prior to injecting into the chillers or washing systems. The carbonic acid is mixed with a chlorinated solution to form hypochlorous acid. The combination of the carbonic acid solution and the chlorinated solution can form up to a 98% hypochlorous acid solution that is injected into the chillers or washing system that will enhance the kill of foodborne pathogens.

Accordingly, it is an object of the present invention to provide a pathogen management system utilizing hypochlorous acid.

It is yet a further object of the present invention to provide a pathogen management system utilizing hypochlorous acid stream at a pH of between about 4.3 and 7.

These and other objects, features and advantages of the present invention will become more apparent upon reading the following specification in conjunction with the accompanying drawing figures.

DETAILED DESCRIPTION OF THE PREFERRED EMBODIMENT

Figure 1:
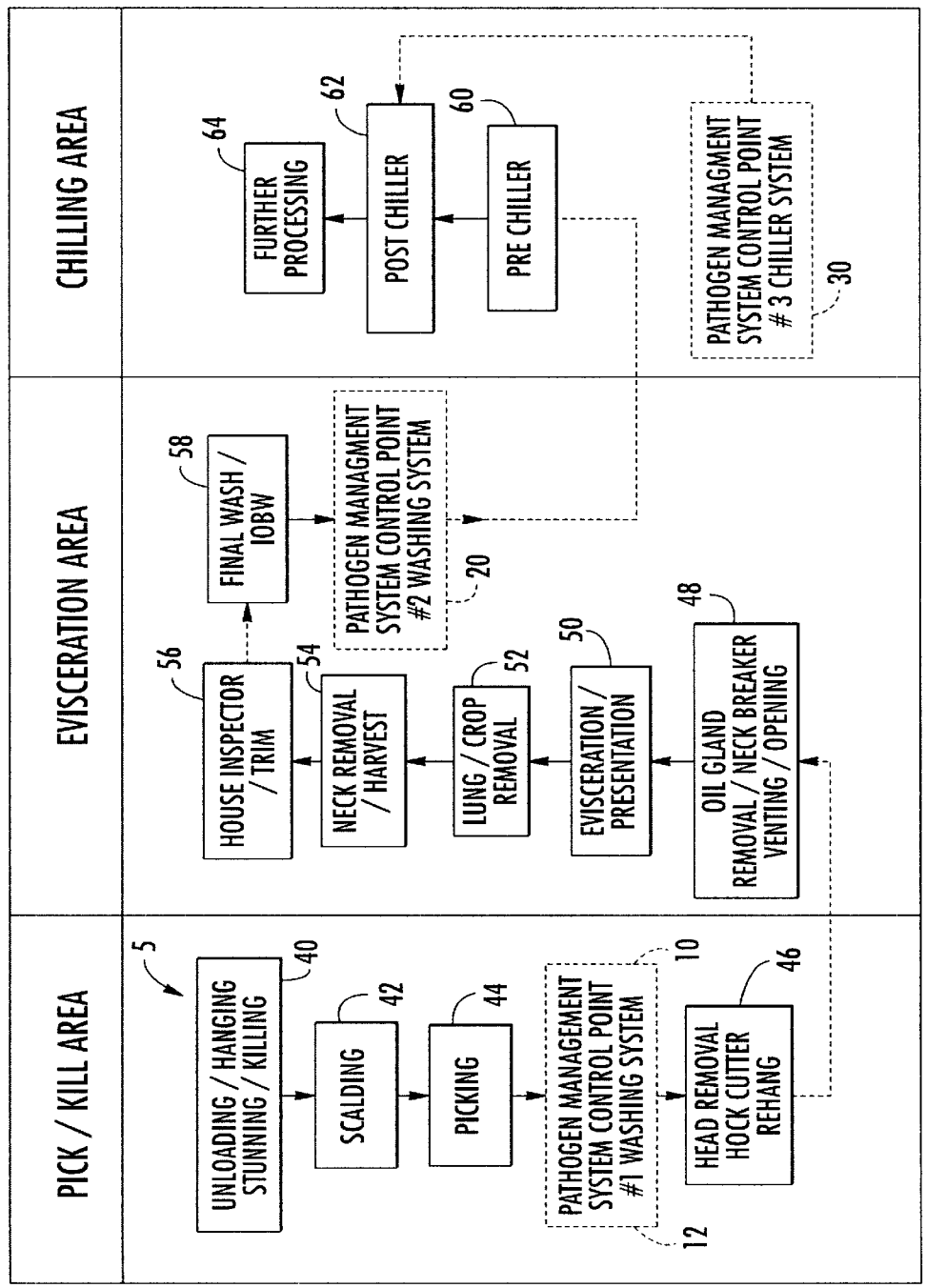
FIG. 1 is block diagram of a preferred embodiment of the present invention in a poultry processing environment.

The present invention incorporates the use of hypochlorous acid as a pathogen control medium. The present pathogen management system preferably comprises utilizing a hypochlorous acid stream of between about 4.3 and 7.0 pH as a pathogen reduction agent. The preferred embodiment of the present invention is utilizing such a hypochlorous acid stream to reduce pathogens in poultry processing plants. It will be understood that the present invention is not so limited to poultry processing, and can be used as a pathogen management system in numerous applications.

In a preferred embodiment, a hypochlorous acid stream is used in more than one discrete location along a poultry processing line, although preliminary investigations for pathogens began as a one-control point approach in the process at the immersion chillers.

The initial testing results came back very positive, but did not completely remove all the pathogens. Samples of chiller water determined that it was sterilized with hypochlorous acid. It appeared that the disinfecting capabilities were maximized at the chiller. The results indicated that pathogens control was necessary in other locations in the plant.

One issue was that the pores are restricted on the carcass by the time the carcass enters the post chiller. This limits the pathogen killing capabilities at the post chiller area. Through preliminary testing, it was determined that the addition of hypochlorous acid should be continued on at least two other locations in conjunction with the chillers for maximum pathogen control. The other two locations are the EVIS area and the Pick/kill Area.

One of the main problems confronting pathogen control at the poultry plant is that the organic load and pathogen load is different on every carcass. A carcass can be cross-contaminated at any location throughout the processing area. This problem would be solved if the pathogens were attacked at each of the three critical control points.

The first chiller test began with the installation of a hypochlorous acid system at a facility in Springdale, Ark. The base line of the test began with a plant that was having an issue with pathogens in the chiller water. This plant, which ran the chillers normally without chlorine, tested positive for Salmonella in the chiller water. They compiled 34 samples over an eight-week period. There were 19 samples returned positive for Salmonella. The foodborne pathogen elimination test began by injecting a calcium hypochlorite solution into the chiller recirculation lines without pH control. The results for pathogen control were better. The results saw a reduction in Salmonella by 40%. This test ran for four weeks.

The plant compiled 83 samples and 16 samples were returned with a positive result of Salmonella. A hypochlorous acid system then was placed on-line to control the pH in the calcium hypochlorite solution. This solution with the reduction of pH formed a 98% hypochlorous acid solution. This hypochlorous acid solution then was injected into the chiller recirculation lines. The plant then compiled 41 samples over a period of three weeks and 2 samples were returned positive. This was an improvement in foodborne pathogen elimination.

Another of the foodborne pathogen elimination tests was coordinated with a facility in Dallas, Tex. This test began with the installation of a hypochlorous acid system in the chiller system. The base line testing began with having an issue with the $E$-$Coli$ pathogen in the immersion chiller water. This plant, which ran the chillers normally with chlorine, tested for $E$-$Coli$ using the standard $E$-$Coli$ testing procedures, twelve times a day. The $E$-$coli$ numbers compiled were acceptable. In January, the plant detected $E$-$Coli$ on 133 samples out of 264. This is a 50% detection rate. In February, the plant detected $E$-$Coli$ on 110 samples out of 240. This is a 45% detection rate. A hypochlorous acid system was installed in-line to control the pH in the calcium hypochlorite solution. This solution with the reduction of pH formed a 98% hypochlorous acid solution. This hypochlorous acid solution then was injected into the chiller recirculation lines. The plant then began compiling more consistent $E$-$Coli$ numbers immediately. Since March, the numbers at this plant have been a majority of zeros (cfu/ml). In March, the plant detected $E$-$Coli$ on 76 samples out of 264. This is a 28% detection rate. 83% of these samples were below 100 cfu/ml. In April, the plant detected $E$-$Coli$ on 37 samples out of 264. This is a 14% detection rate. 99% of these samples were below 100 cfu/ml. In May, the plant detected $E$-$Coli$ on 23 samples out of 276. This is an 8% detection rate. 100% of these samples were below 100 cfu/ml. Since May, the numbers have looked very similar. There have been very few detections of $E$-$Coli$ over 100 cfu/ml.

More tests are being conducted at a facility in Natchitoches, La. The project began by adding hypochlorous acid to the IOBW on-line. Tests were performed on the carcass before and after the IOBW. APC, Coliform and $E$-$Coli$ test were run on the carcass. Average APC of the carcass entering the IOBW was 90,559 cfu/ml, Coliform of 2,103 cfu/ml and $E$-$Coli$ of 1,429 cfu/ml. After adding hypochlorous acid to the existing IOBW, using standard nozzles, a major reduction in the numbers was found. The average APC was 12,792, Coliform 664 cfu/ml and $E.$ $coli$ 383 cfu/ml. This was only with 13 seconds of wash time.

The second stage of this project was to install the hypochlorous acid system on the chiller system. The base line testing began with having an issue with the $E$-$Coli$ pathogen in the immersion chiller water. This plant, which ran the chillers normally with chlorine, tested for $E$-$Coli$ using the standard $E$-$Coli$ testing procedures, eleven times a day. The $E$-$coli$ numbers compiled were OK. As a baseline for this stage, May 2001, 258 $E$-$Coli$ samples were taken. 7% of these samples were over 100 cfu/ml. 55% of these samples were over 10 cfu/ml. In June, 238 samples were taken. Of these 238 sample, 13% samples being over 100 cfu/ml. 66% of these samples were over 10 cfu/ml. Starting July, the numbers look a little better. 254 samples were taken. Of these 254 samples, 5% samples being over 100 cfu/ml. 38% of these samples were over 10 cfu/ml. The numbers were repeated month to month until the pick/kill room hypochlorous acid system was installed. In November, 251 samples were taken. Only one sample was over 100 cfu/ml. 20% of these samples were over 10 cfu/ml. In December, so far 121 samples have been taken. Only two samples were over 100 cfu/ml., 28% of these samples were over 10 cfu/ml.

There was a major improvement on the system by controlling the organic load on the carcass in the pick room. Controlling the incoming organic load of the carcass improves the disinfecting capabilities of the chiller process. There was a dramatic improvement from disinfecting at one control point to disinfecting at two control points.

As the above shows, pathogen reduction was markedly improved through the use of a hypochlorous acid system at various stages of poultry processing. In one embodiment of the present system, a poultry carcass is cleaned within a first washing system located in the pick/kill room. The first washing system comprises a unit powered by two 0.5 HP, fully enclosed, fan cooled, wash down safe 240 or 480 VAC motors. These motors turn one shaft each containing three 12" long and 16" dia. nylon filament PVC core brushes. The shafts are on a diagonal, being high on the entrance end and low on the exit end. A water booster pump is used to provide 70 to 80 psi hypochlorous acid to two main spray headers. Two additional spray headers provide hypochlorous acid at 20 ppm at 30 to 40 psi. The spray headers follow the same angle as the brushes. The different spray nozzles used on each spray header are selected for their spray pattern and gpm usage, and are placed on the headers so as to make contact with the bird in known trouble areas. Total water consumption is approximately 27 gpm. A 3" sanitary pipe on the bottom of the cabinet carries the wastewater to the drain.

Referring now to FIG. 1, a block diagram of a poultry processing line 5 is shown, utilizing three specific locations of application of hypochlorous acid to the process at first washing system 10, second washing system 20 and third washing system 30.

Birds (not shown) enter the processing line 5, and are unloaded, hanged, stunned and killed at step 40. The birds are then scalded 42, picked 44, and enter washing system 10. This first pathogen reduction location 10 is in the pick/kill room. The hypochlorous acid is added to the washing system 10 to clean the organic load off the exterior of the carcass. Unit 12 (also shown in FIG. 2) of washing system 10 is designed to remove external contaminates from whole birds as they are processed and conveyed via the EVIS overhead conveyor system. While the unit 12 reduces water consumption over conventional cleaning methods, it consumes sufficient amounts to effectively clean as designed.

The unit 12 preferably is installed on-line in an exact vertical and left to right position to more fully receive the size and shape of the bird. Measurements of shackle length, shackle centers and height above the floor, as well as, bird weight are used in the custom manufacturing of each unit.

The units 12 are designed to clean each bird using a combination of brushes 14/hypochlorous acid solution action. The hypochlorous acid spray headers sprays onto the brushes 14 to prevent cross-contamination. The main spray headers spray hypochlorous acid onto the bird. As the bird enters the cabinet hung by the hocks, a sheet of hypochlorous acid approximately 80 psi flushes the hock and trailing drum area on the breast side. A second sheet of hypochlorous acid cleans the leading drum area on the backside. At the same time, contact is made by the brushes 14. The brushes 14 rotate down on the breast side and reach into the wing area. Brush 14 on the backside rotates up to more closely follow the contour of the bird and lift the tail. As the bird continues through the unit 12, the brushes and water clean the bird beginning at the top and working toward the bottom.

The birds continue through the process 5 and are further processed through locations 46, 48, 50, 52, 54, 56 and 58 until entering washing system 20. This second pathogen reduction location 20 is located in the post IOBW area. Hypochlorous acid is sprayed on the carcass as it goes through the washer system 20, which may comprise a unit similar to unit 12 of washing system 10. After it exits the washing system 20, the carcass will go to the final trim/inspection station.

The birds continue through the process 5 and are further processed through locations 60, 62 and 64. The third pathogen reduction location 30 is in the chiller area of the process 5, and processed the chiller water used in the post chiller 62. Here, hypochlorous acid is added to the chiller, to maintain free available chlorine in the chilled water.

Figure 2:
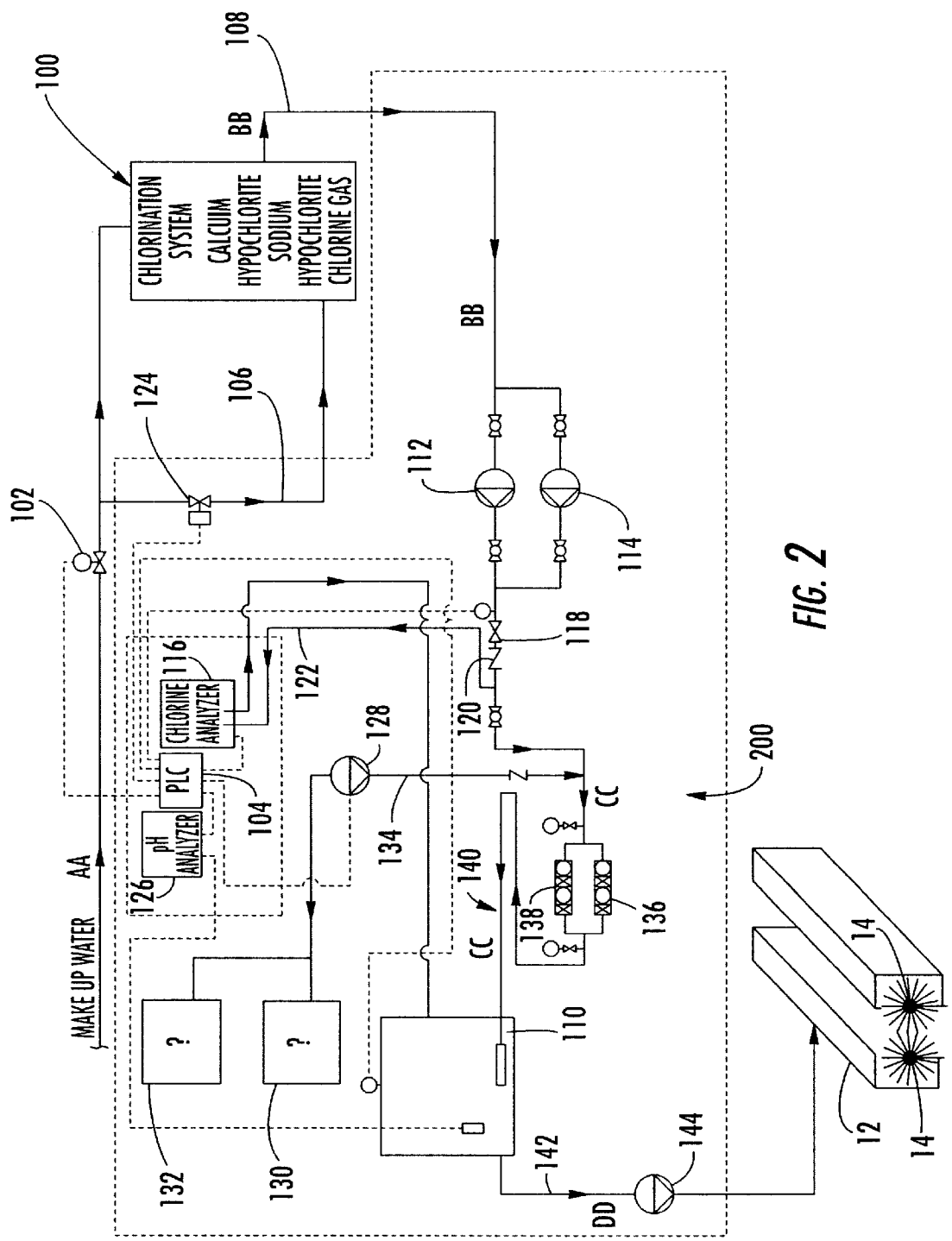
FIG. 2 is a flow diagram of a solution feed system in accordance with a preferred embodiment of the present invention.

The present invention utilizes hypochlorous acid that can be manufactured by a system of generating hypochlorous acid. For example, referring now to FIG. 2, a general schematic of a hypochlorous acid system is shown. As shown in FIG. 2, a stream of make up water AA is directed from a water source to chlorination system 100. Stream AA is typically maintained at normal line pressures. Stream AA flows through shut-off valve 102, and the total flow rate of make up water stream AA is controllable by, for example, the operation of a metering control valve 124 in response to signals from a Programmed Logic Controller (PLC) 104 which coordinates the overall system operation. A line 106 can split a portion of make up water stream AA providing greater control of the fluid volume in the chlorination system 100. The remainder of make up water stream AA enters chlorination system 100 and is subjected to chlorination therein by the addition of a chlorinating agent. The chlorinating agent may be a chlorine gas, a solid hypochlorite salt (e.g., NaOCl or $Ca(OCl)_2$), or a liquid hypochlorite solution (i.e., a bleach). The chlorination agent serves to raise the concentration of chlorine in make up water stream AA in the hypochlorite ion ($OCl^-$), hypochlorous acid (HOCl), or a combination thereof. In one embodiment, the chlorination agent is not a metal chlorite including but not limited to $NaOCl_2$.

Stream AA exits the chlorination system 100 as chlorinated stream BB through line 108 directed to a holding tank 110 through pumps 112 and 114 which increase the pressure of chlorinated water stream BB to at least about 50 psi. A small portion of chlorinated water stream BB can be diverted to a chlorine analyzer 116 from a point just downstream of gate valve 118 and check valve 120 via bypass stream 122. Gate valve 118 and check valve 120 prevent back flow in the system. Chlorine analyzer 116 can sense the chlorine level (ppm) of chlorinated water stream BB and transmits a signal indicative of this level to PLC 104. PLC 104 in turn generates a control signal operate metering control valve 124 to control the fraction of flow AA to maintain chlorinated water stream BB at a desired chlorine concentration. In one exemplary embodiment, the desired chlorine concentration is about 50 ppm or less.

A pH analyzer 126 can sense the pH of chlorinated water stream BB in holding tank 110 and communicates this information to PLC 104. PLC 104 regulates booster pump 128 such that the volume of acid from acidifier systems 130 or 132 increases to maintain the pH acidified chlorinated water stream/hypochlorous acid stream CC in the range of about 4.3 to about 7 resulting in an increase in HOCl concentration compared to $OCl^-$ concentration in holding tank 110 (i.e., the ratio of HOCL to $OCl^-$ is greater than one). Hypochlorous acid stream CC preferably contains about 77 to about 99 percent hypochlorous acid at ambient temperature.

The added acid can be organic or inorganic. Suitable organic acids include formic acid, acetic acid, citric acid, lactic acid, trifluoroacetic acid, oxalic acid, tartaric acid, fumaric acid, maleic acid, methanesulfonic acid, benzenesulfonic acid and p-toluenesulfonic acid. Suitable inorganic acids include, but are not limited to, hydrochloric acid, hydrobromic acid, sulfuric acid, nitric acid and phosphoric acid. The acid stream joins chlorinated stream BB via line 134 upstream of static mixers 136 and 138. In one embodiment, hypochlorous acid stream CC is maintained at a pressure of at least 50 psi. It will be appreciated that the acids can be liquid or solid.

After acid injection, hypochlorous acid stream CC passes through the pair of static mixers 136 and 138 which are arranged in parallel and serve to evenly disperse the acid throughout the hypochlorous acid stream CC. Hypochlorous acid stream CC then optionally passes through a serpentine loop 140 which allows additional contact time for the injected acid to blend into hypochlorous acid stream CC.

Hypochlorous acid stream CC then enters holding tank 110 before injection into a target liquid stream DD via line 142. Pump 144 moves stream DD out of line 142 optionally to a washing system, as shown in FIG. 2 as unit 12 of washing system 10. In one embodiment, stream DD is maintained at a pressure of at least about 50 psi.

The pH analyzer 126 is provided to sense the pH of target liquid stream DD downstream of the point at which the acidified chlorinated carrier water is injected and to provide a signal indicative of the sensed pH to PLC 104. PLC 104 then adjusts the acid flow rate through pump 128 to control the amount of acid being introduced and thereby maintains the pH of target liquid stream DD at a desired setpoint for efficient chlorination as discussed above.

Figure 3:
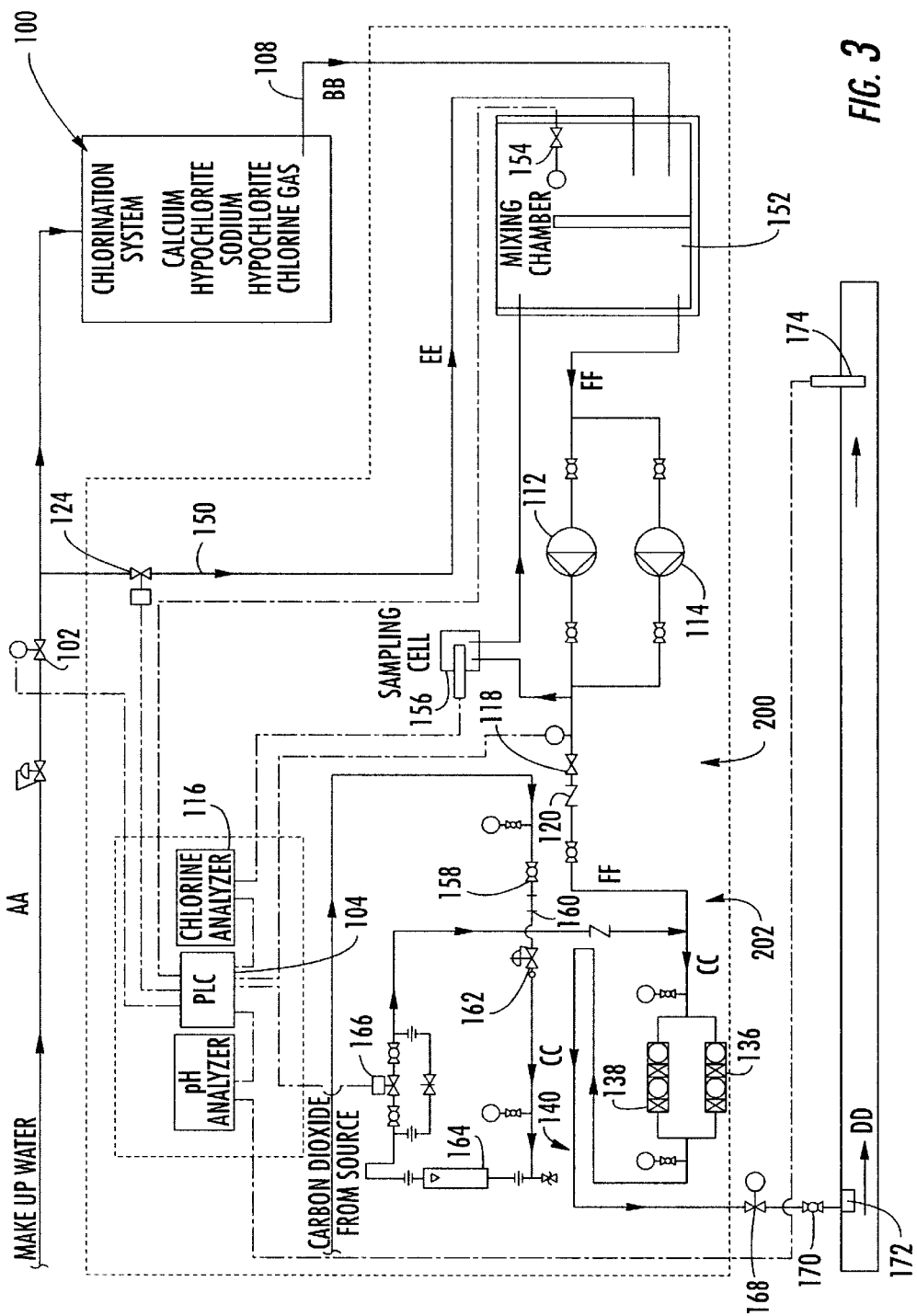
FIG. 3 is a flow diagram of a solution feed system in accordance with another preferred embodiment of the present invention.

In another preferred embodiment of the present invention utilizing a carbon dioxide injection system, as shown in FIG. 3, the stream of make up water AA is directed from a water source to the chlorination system 200. The description of the preferred embodiment of FIG. 2 is not repeated here, as only the differences between the two embodiments are highlighted. It will be understood by those of skill in the art that similar elements of FIGS. 2 and 3 perform the same or similar functions.

In this embodiment, a bypass line 150 diverts a portion of make up water stream AA around chlorination system 100 as a chlorination bypass stream EE. The remainder of make up water stream AA enters chlorination system 100 and is subjected to chlorination therein by the addition of a chlorinating agent. Stream AA exits the chlorination system 100 as chlorinated stream BB through line 108.

Bypass stream EE and chlorination stream BB are both directed into a mixing chamber 152 wherein they are recombined. Mixing chamber 152 includes a level sensor 154 which generates a signal indicative of the water level therein. This signal is relayed to PLC 104 which in turn generates a control signal to control the operation of flow control valve 102 to maintain a desired liquid level in mixing tank 152. Mixing tank 152 is sized to allow time for even mixing of the chlorinated subfraction of chlorination stream BB with bypass stream EE before allowing it to exit as mixed water stream FF.

Mixed water stream FF is directed from mixing chamber 152 through pumps 112 and 114. A small portion of mixed water stream FF can be diverted to a sampling cell 156, or directly to chlorine analyzer 116. Chlorine analyzer 116/Sampling cell 156 can sense the chlorine level (ppm) of mixed water stream FF and transmit a signal indicative of this level to PLC 104. PLC 104 in turn generates a control signal operate metering control valve 102 to control the fraction of flow BB which passes through bypass line 150 to maintain mixed water stream FF at a desired chlorine concentration.

Mixed water stream FF next passes to acid injection system 200 being a carbon dioxide injection system 202 through gate valve 118 and check valve 120. In its simplest form, carbon dioxide injection system 202 includes a regulated flow of pressurized $CO_2$ which is injected into mixed water stream FF at a pressure significantly higher than that of mixed water stream FF. In one preferred embodiment, the carbon dioxide gas is directed through an isolation ball valve 158 then a wye strainer 160, then a pressure reduction valve 162. After pressure reduction valve 162, the carbon dioxide gas goes through a flow meter 164 and a $CO_2$ metering control valve 166 that is responsive to maintain the $CO_2$ flow at a desired rate as determined by PLC 104.

In a preferred embodiment, mixed water stream FF is maintained at greater than or equal to 50 psi at the $CO_2$ injection point and the $CO_2$ is maintained at a minimum of 55–75 psi or at least approximately 10 psi greater than the pressure of mixed water stream FF.

Hypochlorous acid stream CC then passes through a full port ball valve 170 before injection into a target liquid stream DD via diffuser 172. Diffuser 172 is designed to maintain system pressure, thus forcing the $CO_2$ gas to remain in solution in the hypochlorous acid stream CC.

In a preferred embodiment, the pressure of target liquid stream DD is less than that of the hypochlorous acid stream CC. Therefore, as the hypochlorous acid stream CC passes through the small holes in diffuser 172, it is diffused into target liquid stream DD, thereby lowering the pH of target liquid stream DD and shifting the hyopchlorite/hypochlorous acid balance to form predominantly hypochlorous acid.

A pH sensor 174 can be provided to sense the pH of target liquid stream DD downstream of the point at which the hypochlorous acid stream CC is injected and to provide a signal indicative of the sensed pH to PLC 104. PLC 104 then adjusts the $CO_2$ flow rate through $CO_2$ metering valve 166 to control the amount of carbonic acid being introduced and thereby maintains the pH of target liquid stream DD at a desired setpoint for efficient chlorination as discussed above.

Figure 4:
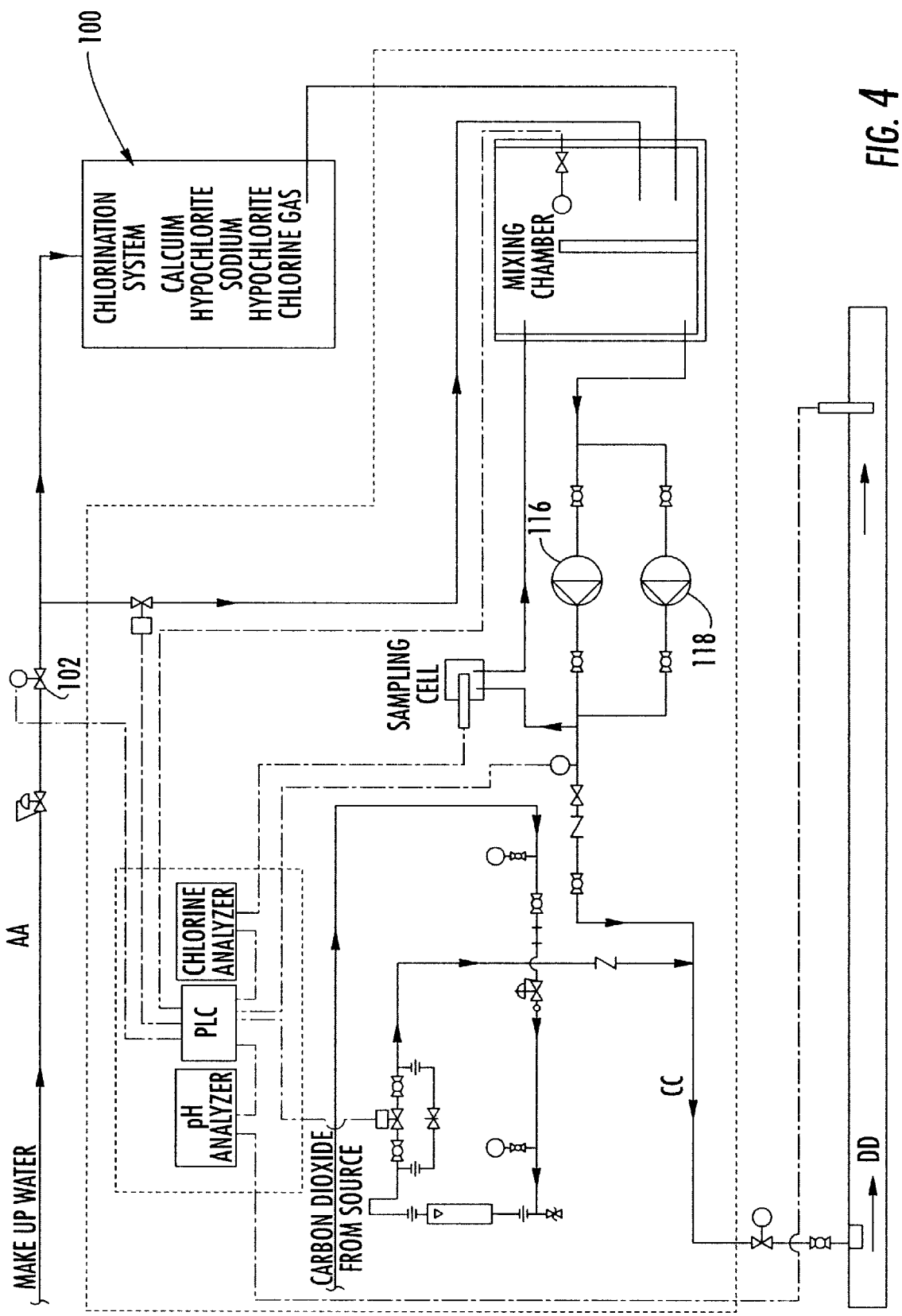
FIG. 4 is a flow diagram of a solution feed system in accordance with another preferred embodiment of the present invention.

As shown in FIG. 4, in an alternative embodiment, hypochlorous acid stream CC may also be added directly to target liquid stream DD immediately after injection of carbon dioxide gas. In this embodiment, the carbon dioxide gas will still be largely present in gaseous form because there are no static mixers or serpentine loop to provide additional mixing and time to allow the carbon dioxide to go into solution. A substantial portion of the carbon dioxide will still go into solution as carbonic acid in the target liquid stream as it flows to its end use.

As previously mentioned, in the treated water solution, $HOCl$ and $OCl^-$ are generally present in a pH dependent equilibrium:

$$HOCl \Leftrightarrow H^+ + OCl^- \quad pKa = 7.53$$

As shown in Table 1, at low pH, HOCl is the predominant form, while at high pH, $OCl^-$ predominates:

TABLE 1

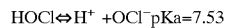

| pH\Temp °C. | 0 | 5 | 10 | 15 | 20 | 25 | 30 |
|---|---|---|---|---|---|---|---|
| 5.0 | 99.85 | 99.83 | 99.80 | 99.77 | 99.74 | 99.71 | 99.68 |
| 5.5 | 99.53 | 99.75 | 99.36 | 99.27 | 99.18 | 99.09 | 99.01 |
| 6.0 | 98.53 | 98.28 | 98.01 | 97.73 | 97.45 | 97.18 | 96.92 |
| 7.0 | 87.05 | 85.08 | 83.11 | 81.17 | 79.23 | 77.53 | 75.90 |
| 8.0 | 40.19 | 36.32 | 32.98 | 30.12 | 27.62 | 25.65 | 23.95 |
| 9.0 | 6.30 | 5.40 | 4.69 | 4.13 | 3.68 | 3.34 | 3.05 |
| 10.0 | 0.67 | 0.57 | 0.49 | 0.43 | 0.38 | 0.34 | 0.31 |
| 11.0 | 0.067 | 0.057 | 0.049 | 0.043 | 0.038 | 0.034 | 0.031 |

The HOCl is much more effective than $OCl^-$ for killing microorganisms because HOCl is nonpolar and can cross the outer membrane of most microbes and bacteria. Therefore, it is desirable to control the pH of the treated water solution to between 4.3 and 7.0, and more preferable to between 6.0 and 6.2 in order to ensure almost complete (~98%) conversion to the hypochlorous acid form and thereby increase the antimicrobial effectiveness of the chlorination of the target liquid stream. At a pH of about 4.3 or lower, chlorine gas evolves from the solution. Therefore, in one embodiment, the pH of the solution stream is greater than about 4.3 to about 7.

The present pathogen management system meets and/or exceeds the performance standards for pathogens control according to the FSIS standards (*E-Coli*-9 CFR 381.94 (a), Salmonella—9 CFR 381.94 (b)). Further, the present invention meets the strict compliance of standards to be used for on-line reprocessing as stated FSIS Poultry Products Inspection Regulations (9 CFR 381 .9 1). This system will maintain zero fecal contamination of the carcass according to (9 CFR 381.65) and maintain existing pre chill finish product standard (9 CFR 381.76).

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. In a system to control pathogens on a target element, the system including subjecting the target element to a pathogen reducing agent, the improvement comprising subjecting the target element to hypochlorous acid formed by the following steps:
   (a) combining an acid with a first carrier stream to form a first mixed stream;
   (b) introducing a chlorination agent into a control stream, the chlorination agent increasing the concentration of hypochlorous acid and hypochlorite of the control stream;
   (c) combining the first mixed stream with the control stream having the chlorination agent to form the hypochlorous acid stream, wherein about 77 to about 99 percent of the chlorination agent in the hypochlorous acid stream is hypochlorous acid.

2. The system of claim 1, wherein the target element is a poultry product.

3. The system of claim 1, wherein after combining the first mixed stream with the control stream, the pH of the hypochlorous acid stream is between approximately 4.3 and approximately 7.0.

4. The system of claim 1, wherein the first mixed stream is pressurized.

5. The system of claim 1, wherein the control stream with a chlorination agent is pressurized.

6. The system of claim 1, wherein the acid includes carbon dioxide.

7. The system of claim 1, wherein the first carrier stream is pressurized to at least about 50 psi.

8. The system of claim 1, wherein the target element is a food item.

9. In a system for controlling pathogens during the processing of animals into food including conveying an animal carcass through processing equipment, the improvement comprising subjecting the animal carcass to hypochlorous acid formed by the following steps;
   (a) acidifying a first carrier stream to form a first mixed stream, wherein the first mixed stream comprises carbonic acid;
   (b) introducing a chlorination agent into a control stream, the chlorination agent increasing the concentration of hypochlorous acid and hypochlorite of the control stream;
   (c) combining the first mixed stream with the control stream having the chlorination agent to form the hypochlorous acid stream.

10. The system of claim 9, wherein the hypochlorous acid is in the form of a hypochlorous acid stream of between about 4.3 and 7.0 pH.

11. The system of claim 9, wherein the animal carcass is conveyed through a pick/kill area, wherein the animal carcass is subjected to a hypochlorous acid stream in the pick/kill area.

12. The system of claim 9, wherein the animal carcass is conveyed through an evisceration area, wherein the animal carcass is subjected to a hypochlorous acid stream in the evisceration area.

13. The system of claim 12, wherein the animal carcass also is conveyed through an evisceration area, wherein the animal carcass is subjected to a hypochlorous acid stream in the evisceration area.

14. The system of claim 13, wherein the animal carcass also is conveyed through a chilling area, wherein the animal carcass is subjected to a hypochlorous acid stream in the chilling area.

15. The system of claim 9, wherein the animal carcass is conveyed through a chilling area, wherein the animal carcass is subjected to a hypochlorous acid stream in the chilling area.

16. The system of claim 9, wherein the target element is a food item.

17. A method to control pathogens on a target element, the method comprising the following steps:
   (a) combining an acid with a pressurized first carrier stream to form a pressurized first mixed stream;
   (b) introducing a chlorination agent into a control stream, the chlorination agent increasing the concentration of hypochlorous acid and hypochlorite of the control stream;
   (c) combining the first pressurized mixed stream with the control stream having the chlorination agent to form the hypochlorous acid stream; and
   (d) contacting said target element with the hypochlorous acid stream.

18. The method of claim 17, wherein the target element is selected from the group consisting of an animal and a carcass.

19. The method of claim 17, wherein the target element is conveyed through a pick/kill area, wherein the target element is subjected to a hypochlorous acid stream in the pick/kill area.

20. The method of claim 17, wherein the target element is conveyed through an evisceration area, wherein the target element is subjected to a hypochlorous acid stream in the evisceration area.

21. The method of claim 17, wherein the target element is conveyed through a chilling area, wherein the target element is subjected to a hypochlorous acid stream in the chilling area.

22. The method of claim 17, wherein the target element also is conveyed through a chilling area, wherein the target element is subjected to a hypochlorous acid stream in the chilling area.

23. The method of claim 17, wherein the pH of the hypochlorous acid stream is between approximately 4.3 and approximately 7.0.

24. The method of claim 17, wherein the target element is a food item.

25. In a system to control pathogens on a target element, the system including subjecting the target element to a pathogen reducing agent, the improvement comprising subjecting the target element to hypochlorous acid formed by the following steps:
   (a) forming an acid in a first carrier stream to form a first mixed stream;

(b) introducing a chlorination agent into a control stream, the chlorination agent increasing the concentration of hypochlorous acid and hypochlorite of the control stream, and wherein the control stream with the chlorination agent is pressurized;

(c) combining the first mixed stream with the pressurized control stream having the chlorination agent to form the hypochlorous acid stream; and (d) contacting said target element with the hypochlorous acid stream.

26. The method of claim 25, wherein the target element is selected from the group consisting of an animal and a carcass.

27. The system of claim 25, wherein the target element is conveyed through a pick/kill area, wherein the target element is subjected to a hypochlorous acid stream in the pick/kill area.

28. The system of claim 25, wherein the target element is conveyed through an evisceration area, wherein the target element is subjected to a hypochlorous acid stream in the evisceration area.

29. The system of claim 25, wherein the target element is conveyed through a chilling area, wherein the target element is subjected to a hypochlorous acid stream in the chilling area.

30. The system of claim 25, wherein the target element also is conveyed through an evisceration area, wherein the target element is subjected to a hypochlorous acid stream in the evisceration area.

31. The system of claim 25, wherein the target element also is conveyed through a chilling area, wherein the target element is subjected to a hypochlorous acid stream in the chilling area.

32. The system of claim 25, wherein the target element is a food item.

* * * * *

(12) INTER PARTES REEXAMINATION CERTIFICATE (0156th)

United States Patent
Shane et al.

(10) Number: US 6,605,308 C1
(45) Certificate Issued: May 4, 2010

(54) PATHOGEN MANAGEMENT SYSTEM

(75) Inventors: Tommy J. Shane, Loganville, GA (US); Harvey Swain, Lawrenceville, GA (US)

(73) Assignee: Tomco2 Equipment Company, Loganville, GA (US)

Reexamination Request:
No. 95/000,302, Sep. 17, 2007

Reexamination Certificate for:
Patent No.: 6,605,308
Issued: Aug. 12, 2003
Appl. No.: 10/050,492
Filed: Jan. 16, 2002

Related U.S. Application Data

(60) Provisional application No. 60/316,047, filed on Aug. 30, 2001, and provisional application No. 60/261,923, filed on Jan. 16, 2001.

(51) Int. Cl.
| | |
|---|---|
| A23B 4/30 | (2006.01) |
| A23B 4/14 | (2006.01) |
| A23B 4/24 | (2006.01) |
| A23B 4/26 | (2006.01) |
| A61L 2/00 | (2006.01) |
| C02F 1/00 | (2006.01) |
| C02F 1/66 | (2006.01) |
| C02F 1/76 | (2006.01) |

(52) U.S. Cl. ............ 426/332; 426/532; 134/25.3; 134/26; 452/123; 452/131

(58) Field of Classification Search .................. None
See application file for complete search history.

(56) References Cited

U.S. PATENT DOCUMENTS 6,605,253 B1   8/2003   Perkins

OTHER PUBLICATIONS

U.S. Appl. No. 60/138,368, filed Jun. 10, 1999, Perkins.
White, Geo. Clifford, "Handbook of Chlorination and Alternative Disinfectants—Third Edition" Van Nostrand Reinhold (International Thomson Publishing Inc.) (New York) (1992), pp. 184–193, 230–233, 246–249.

*Primary Examiner*—Sharon L Turner

(57) ABSTRACT

A system to control pathogens on a target element is disclosed, wherein the target element is subjected to hypochlorous acid. The present invention incorporates the use of hypochlorous acid as a pathogen control medium, wherein a hypochlorus acid stream of between about 4.3 and 7.0 pH as a pathogen reduction agent is utilized. In one embodiment, the hypochlorous acid stream is used to reduce pathogens in poultry processing plants.

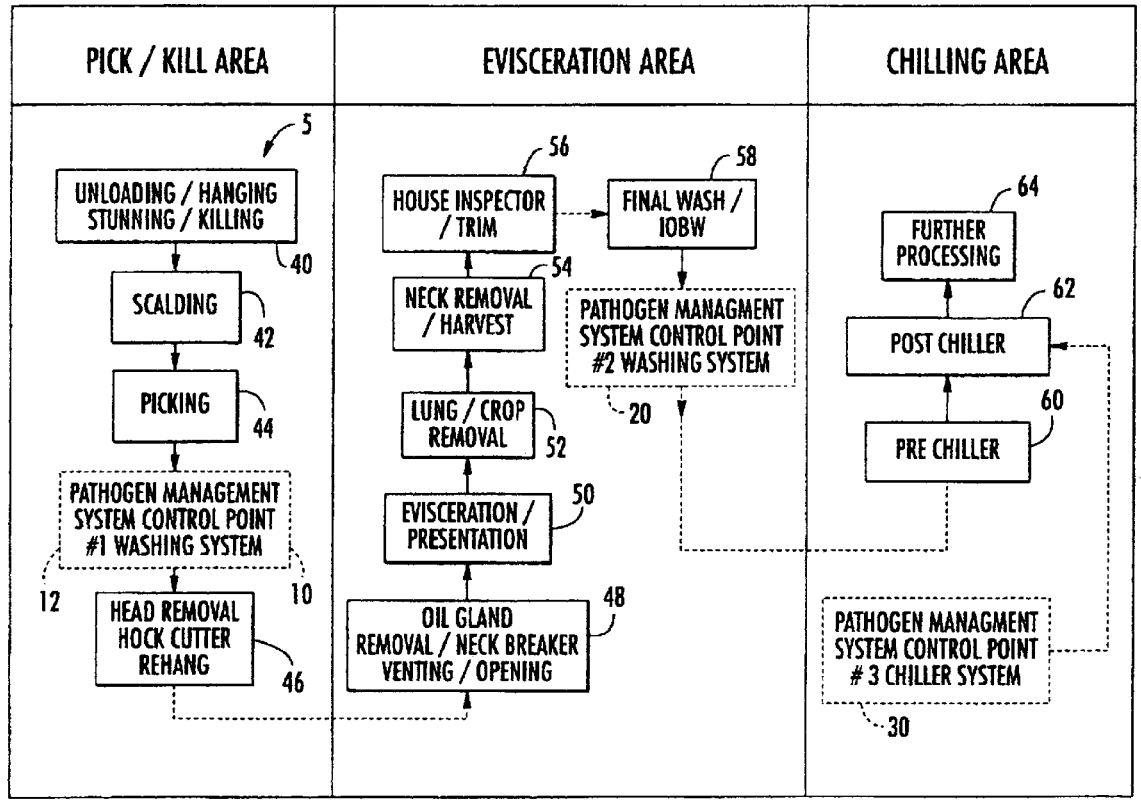

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–5, 8, 17–18, 20, 23–26, 28 and 32 are cancelled.

Claims 6, 7, 9–16, 19, 21, 22, 27 and 29–31 were not reexamined.

\* \* \* \* \*